(12) United States Patent
Sommerlade et al.

(10) Patent No.: US 7,470,819 B2
(45) Date of Patent: Dec. 30, 2008

(54) PROCESS FOR PREPARING ACYLPHOSPHANES AND THEIR OXIDES AND SULPHIDES

(75) Inventors: Reinhard H. Sommerlade, Neuenburg am Rhein (DE); Katharina Fritzsche, Weil am Rhein (DE); Walter Fischer, Reinach (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 11/795,059

(22) PCT Filed: Jan. 9, 2006

(86) PCT No.: PCT/EP2006/050081

§ 371 (c)(1), (2), (4) Date: Jul. 11, 2007

(87) PCT Pub. No.: WO2006/074983

PCT Pub. Date: Jul. 20, 2006

(65) Prior Publication Data

US 2008/0071115 A1    Mar. 20, 2008

(30) Foreign Application Priority Data

Jan. 17, 2005 (EP) .................... 05100253

(51) Int. Cl.
    C07F 9/02 (2006.01)
(52) U.S. Cl. .......................................... 568/8
(58) Field of Classification Search ........ 568/8
    See application file for complete search history.

(56) References Cited

U.S. PATENT DOCUMENTS

| | | | |
|---|---|---|---|
| 4,737,593 A * | 4/1988 | Ellrich et al. .......... | 568/15 |
| 4,792,632 A * | 12/1988 | Ellrich et al. .......... | 568/15 |
| 6,020,528 A | 2/2000 | Leppard et al. ........ | 568/15 |
| 6,888,031 B1 | 5/2005 | Leppard et al. ........ | 568/14 |
| 7,230,137 B2 | 6/2007 | Grutzmacher et al. .... | 568/9 |
| 2004/0204613 A1 | 10/2004 | Wolf et al. ............ | 568/14 |
| 2006/0229469 A1* | 10/2006 | Huttenloch et al. ..... | 562/876 |
| 2006/0247436 A1* | 11/2006 | Sommerlade et al. .... | 544/157 |

FOREIGN PATENT DOCUMENTS

| | | |
|---|---|---|
| GB | 2 310 855 | 9/1997 |
| WO | 00/32612 | 6/2000 |
| WO | 03/019295 | 3/2003 |
| WO | 2004/050668 | 6/2004 |
| WO | 2006/056541 | 6/2006 |

OTHER PUBLICATIONS

Reiter et al., Insignificance of P-HoooP Hydrogen Bonding: Structural Chemistry of Neutral and Protonated 1,8-Di(phosphinyl)naphthalene, Journal of the American Chemical Society (2004), 126(48), 15833-15843.*
Patent abstracts of Japan, vol. 2000, No. 04, (Aug. 2000) of JP 2000007689.
Bourumeau et al.; Journal of Organometallic Chemistry vol. 529 No. 1 (Feb. 1997) pp. 205-213.
F. Pass et al.; Monatshefte fur Chemie, vol. 90, Jan. 1959, pp. 148-156.
Mann et al; Journal of the Chemical Society, 1952, pp. 3039-3046.
D. Fenske et al.; Chemische Berichte; vol. 109, 1976, pp. 359-362.

* cited by examiner

*Primary Examiner*—Daniel M Sullivan
*Assistant Examiner*—Chukwuma O Nwaonicha
(74) *Attorney, Agent, or Firm*—Joseph C. Suhadolnik

(57) ABSTRACT

A process for the preparation of bis-acylphosphanes of formula $R^1P(COR^2)_2$ wherein $R^1$ is unsubstituted phenyl or phenyl substituted by one to five halogen, $C_1$-$C_8$-alkyl, $C_1$-$C_8$-alkylthio and/or $C_1$-$C_8$-alkoxy; $R^2$ is $C_1$-$C_{18}$-alkyl or $C_2$-$C_{18}$-alkenyl; $C_1$-$C_{18}$-alkyl or $C_2$-$C_{18}$-alkenyl substituted once or more than once by halogen —$OR^{10}$, —OCO—$R^{10}$, —OCO-Hal, —COO—$R^{10}$, —N($R^{11}$)—CO—$R^{10}$, —N($R^{11}$)—CO-Hal, —CO—NR$^{11}$R$^{10}$, —CH=CH—CO—$OR^{10}$ or —CH=CH-phenyl; —C($C_1$-$C_4$alkyl)=C($C_1$-$C_4$alkyl)-CO—$OR^{10}$ or —C($C_1$-$C_4$alkyl)=C($C_1$-$C_4$alkyl)-phenyl; $C_5$-$C_{12}$cycloalkyl, $C_2$-$C_{18}$alkenyl, phenyl-$C_1$-$C_4$alkenyl, phenyl, naphthyl, biphenyl or a 5- or 6-membered —O—, S— or N-containing heterocyclic ring, the radicals phenyl, naphthyl, biphenyl or the 5- or 6-membered -0-, S— or N-containing heterocyclic ring being unsubstituted or substituted by one to five halogen, $C_1$-$C_8$alkyl, $C_1$-$C_8$alkoxy and/or $C_1$-$C_8$alkylthio; the process comprises the steps in a) selective reduction of dichlorophenylphosphanes of the formula $R^1P(CI)_2$ by means of hydrogen at a temperature in the range from 20 to 200° C. and under hydrogen pressure of atmospheric pressure to 20 bar in the presence of a hydrogenation catalyst, a tert. aliphatic amine or an aromatic amine and in the presence of a non protic solvent which is unreactive under the hydrogenation conditions to obtain cyclic phenylphosphanes $(R^1P)_n$ (n=4 to 6); or b) selective reduction of $R^1P(CI)_2$ by means of hydrogen at a temperature in the range from 80 to 250° C. and under hydrogen pressure of 25 to 250 bar in the presence of a hydrogenation catalyst, a tert. aliphatic amine or an aromatic amine and in the presence of a non protic solvent which is unreactive under the hydrogenation conditions to obtain $R^1PH_2$; c) subsequent reaction with an acid halide of formula in the presence of an apropriate base $R^2$COHal wherein $R^2$ is as defined above.

19 Claims, No Drawings

PROCESS FOR PREPARING ACYLPHOSPHANES AND THEIR OXIDES AND SULPHIDES

The present invention relates to a new, selective process for the preparation of bisacylphosphanes, bisacylphosphane oxides or bisacylphosphane sulfides.

Methods of industrial Bapo synthesis are based on acylation of in situ prepared phenylphosphanes or its alkali salt as a key step. Due to its dangerous properties such as high toxicity and pyrophoric character, phenylphosphane is not available as a raw material on the market anymore.

The European Patent Publication WO00/32612 corresponding to EP1 135 399 B1 describes a process for the preparation of bisacylphosphanes, bisacylphosphane oxides and of bisacylphosphane sulfides, which process comprises first reacting organic P-monohalogenophosphanes or P, P-dihalogenophosphanes or mixtures thereof, with an alkali metal or magnesium in combination with lithium, where appropriate in the presence of a catalyst, and then carrying out the reaction with acid halides and, in the case of the process for the preparation of oxides, carrying out an oxidation step and, in the case of the preparation of sulfides, reacting the phosphanes so obtained with sulfur. WO00/32612 uses the same starting materials as the presently claimed process but does not proceed via the hydride instead of a metal salt before reaction with the acid chloride.

The British Publication GB2310855 describes the preparation of methylphenylphosphine by lithium aluminium hydride reduction of 4-methylphenyldiethylphosphonate.

The International Publication WO05/014605, describes a process to prepare bisacylphosphanes, which process comprises first reacting organic P-monohalogenophosphanes ($R^2PCl$) or P,P-dihalogenophosphanes ($RPCl_2$), or phosphorus halide oxide or phosphorus halide sulfide with an alkali metal (metallation) in a solvent in the presence of a proton source (reduction), and where appropriate in the presence of a catalyst, and then carrying out the reaction with acid halides.

The European Patent Application EP 04105987.4 describes a process to prepare bisacylphosphanes, which process comprises first reducing elemental phosphorous or $P(Hal)_3$ with sodium to obtain sodium phosphide $Na_3P$, then adding a sterically hindered alcohol to obtain sodium phosphides $NaPH_2$; subsequent reaction with two equivalents of an acid halide $HalCOR^2$ to obtain sodium bisacylphosphide [$R^2CO-P=C(ONa)R^2$]. After the reaction with an electrophilic agent $R^1Hal$ mono- or bisacylphosphanes are obtained.

The International Publication WO04/050668 describes a process to prepare cycloorganyl phosphanes of the formula $(R^1P)_n$ by reacting $R^1PHal_2$ with an alkali metal or an alkaline-earth metal in an organic solvent such as toluene in the presence of an activator.

The Japanese Publication JP 2000 007689 is addressed to the problem of phosphane preparation. Mono-chlorodiphenylphosphanes are hydrogenated in the presence of N,N-dimethylformamide and an amine. The process has the drawback that phenylphosphane cannot be obtained starting from dichlorophenylphosphanes as shown in the comparative example.

Accordingly, there still remains a need for a process to produce acylphosphanes starting from dichlorophenylphosphanes.

The invention relates to a process for the preparation of bis-acylphosphanes of formula I $R^1P(COR^2)_2$ 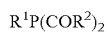

wherein $R^1$ is unsubstituted phenyl or phenyl substituted by one to five halogen, $C_1$-$C_8$-alkyl, $C_1$-$C_8$-alkylthio and/or $C_1$-$C_8$-alkoxy;

$R^2$ is $C_1$-$C_{18}$-alkyl or $C_2$-$C_{18}$-alkenyl; $C_1$-$C_{18}$-alkyl or $C_2$-$C_{18}$-alkenyl substituted once or more than once by halogen —$OR^{10}$, —OCO—$R^{10}$, —OCO-Hal, —COO—$R^{10}$, —N($R^{11}$)—CO—$R^{10}$, —N($R^{11}$)—CO-Hal, —CO—$NR^{11}R^{10}$, —CH=CH—CO—$OR^{10}$ or —CH=CH-phenyl; —C($C_1$-$C_4$-alkyl)=C($C_1$-$C_4$-alkyl)-CO—$OR^{10}$ or —C($C_1$-$C_4$-alkyl)=C($C_1$-$C_4$-alkyl)-phenyl; $C_5$-$C_{12}$-cycloalkyl, $C_2$-$C_{18}$-alkenyl, phenyl-$C_1$-$C_4$-alkyl, phenyl, naphthyl, biphenyl or a 5- or 6-membered —O—, S— or N-containing heterocyclic ring, the radicals phenyl, naphthyl, biphenyl or the 5- or 6-membered —O—, S— or N-containing heterocyclic ring being unsubstituted or substituted by one to five halogen, $C_1$-$C_8$-alkyl, $C_1$-$C_8$-alkoxy and/or $C_1$-$C_8$-alkylthio;

$R^{10}$ is hydrogen, $C_1$-$C_{18}$-alkyl, or $C_2$-$C_{18}$-alkyl which is interrupted by one or several non-successive —O-atoms, $C_5$-$C_{12}$-cycloalkyl, phenyl-$C_1$-$C_4$-alkyl, $C_2$-$C_{18}$-alkenyl, phenyl, naphthyl or biphenyl being unsubstituted or substituted by one to five $C_1$-$C_8$-alkyl, $C_1$-$C_8$-alkoxy, $C_1$-$C_8$-alkylthio and/or halogen;

$R^{11}$ is hydrogen, $C_1$-$C_{18}$-alkyl, $C_2$-$C_{18}$-alkyl which is interrupted by one or several non-successive O atoms, $C_5$-$C_{12}$-cycloalkyl, $C_2$-$C_{18}$-alkenyl, phenyl-$C_1$-$C_4$-alkyl, phenyl, naphthyl, pyridyl, the radicals phenyl, naphthyl or pyridyl being unsubstituted or substituted by one to five $C_1$-$C_8$-alkyl, $C_1$-$C_8$-alkoxy, $C_1$-$C_8$-alkylthio and/or halogen;

the process comprises the steps in a) selective reduction of dichlorophenylphosphanes of the formula II $R^1P(Cl)_2$ 

by means of hydrogen at a temperature in the range from 20 to 200° C. and under hydrogen pressure of atmospheric pressure to 20 bar in the presence of a hydrogenation catalyst, a tert. aliphatic amine or an aromatic amine and in the presence of a non protic solvent which is unreactive under the hydrogenation conditions to obtain cyclic phenylphosphanes $(R^1P)_n$ (n=4 to 6); or b) selective reduction of $R^1P(Cl)_2$ by means of hydrogen at a temperature in the range from 80 to 250° C. and under hydrogen pressure of 25 to 250 bar in the presence of a hydrogenation catalyst, a tert. aliphatic amine or an aromatic amine and in the presence of a non protic solvent which is unreactive under the hydrogenation conditions to obtain $R^1PH_2$;

c) subsequent reaction with an acid halide of formula III in the presence of an appropriate Base $R^2COHal$ 

wherein $R^2$ is as defined above.

The phenylphosphanes are obtained in high yield and with high selectivity. Furthermore it is possible to stop the reaction at an intermediate stage with selective formation of cyclic phenylphosphanes, potentially valuable compound for further transformations.

If two different acid halides are used R²COHal and R²'COHal it is possible to prepare unsymmetric bisacylphosphanes of the formula I'

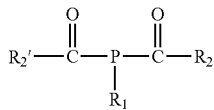

wherein R²' is one of the radicals defined under R², but with the proviso that R² is not equal R²'.

DEFINITIONS $C_1$-$C_{18}$-alkyl is linear or branched and is, for example, $C_1$-$C_{12}$—, $C_1$-$C_8$—, $C_1$-$C_6$— or $C_1$-$C_4$alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl, dodecyl, tetra-decyl, pentadecyl, hexadecyl, heptadecyl or octadecyl.

$C_2$-$C_{18}$-alkenyl radicals may be mono- or polyunsaturated, linear or branched and are, for example, vinyl, allyl, methallyl, 1,1-dimethylallyl, propenyl, butenyl, pentadienyl, hexenyl or octenyl, preferably vinyl or allyl.

$C_5$-$C_{12}$Cycloalkyl is, for example, cyclopentyl, cyclohexyl, cyclooctyl, cyclododecyl, preferably cyclopentyl and cyclohexyl, more preferably cyclohexyl.

$C_1$-$C_8$-alkoxy is linear or branched radicals and is typically methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-ethylhexyloxy or octyloxy, preferably methoxy, ethoxy, propoxy, isopropoxy, n-butyloxy, sec-butyloxy, isobutyloxy, tert-butyloxy, most preferably methoxy.

Halogen (=Hal) is fluoro, chloro, bromo and iodo, preferably chloro and bromo, most preferably chloro.

Examples of —O—, S— or N-containing 5- or 6-membered heterocyclic rings are furyl, thienyl, pyrrolyl, oxinyl, dioxinyl or pyridyl. The cited heterocyclic radicals may be substituted by one to five, e.g. by one or two, linear or branched $C_1$-$C_8$-alkyl, halogen and/or $C_1$-$C_8$-alkoxy. Examples of such compounds are dimethylpyridyl, dimethylpyrrolyl or methylfuryl.

Substituted phenyl, naphthyl or biphenyl is substituted by one to five, e.g. by one, two, three or four, preferably by one, two or three, for example linear or branched $C_1$-$C_8$-alkyl, linear or branched $C_1$-$C_8$-alkoxy or by halogen.

Preferred substituents for phenyl, naphthyl and biphenyl are $C_1$-$C_4$-alkyl, e.g. methyl, $C_1$-$C_4$-alkoxy, e.g. methoxy, and chloro. Particularly preferred substituents are, for example, 2,4,6-trimethylphenyl, 2,6-dichlorophenyl, 2,6-dimethylphenyl or 2,6-dimethoxyphenyl. R² is, for example, $C_1$-$C_{18}$-alkyl or phenyl, preferably 2,4,6-trimethylphenyl, 2,6-dimethylphenyl or 2,6-dimethoxyphenyl, tert-butyl, 1,1-diphenylethyl, 2-phenylpropyl, 2-methylbutyl, 2-methylpentyl, most preferably 2,4,6-trimethylphenyl.

Preferably $R^1$ is unsubstituted phenyl.

Compounds to be highlighted in the above processes are those of formula I, wherein R² is phenyl which is substituted in 2,6- or 2,4,6-position by $C_1$-$C_4$-alkyl and/or $C_1$-$C_4$-alkoxy.

The hydrogenation catalyst is a reduction catalyst. Preferred catalysts include, but are not limited to, ruthenium (Ru), rhenium (Re), rhodium (Rh), platinum (Pt), palladium (Pd), copper (Cu), nickel (Ni), cobalt (Co), molybdenum (Mo), copper chromite, including various oxides and Raney forms thereof. Supports may include carbon (C), niobium (Nb), titania ($TiO_2$), zirconia ($ZrO_2$), silica ($SiO_2$), tin (Sn), alumina ($Al_2O_3$) or mixtures thereof. Especially preferred catalysts include palladium on carbon and palladium on alumina.

Suitable amounts are 0.5 wt % to 30 wt % Pd, preferably 5 wt % to 10 wt %.

The term "tertiary amine" among others includes alkylamines such as: triethylamine, tributylamine, benzyldialkylamine, N-alkylmorpholine, N-alkylpiperidine, N-alkylpyrrolidine, or aromatic amines such as pyridine, 2 or 3 or 4-methylpyridine, 2,3 or 2,4 or 2,5 or 2,6 or 3,4or 3,5-dimethylpyridine, N,N-dialkylaniline, e.g. N,N-dimethylaniine, or mixtures thereof. Preferred is pyridine or triethylamine, especially preferred is pyridine.

The term "non-protic solvent which is unreactive under hydrogenation reactions" refers to aromatic hydrocarbons such as benzene, toluene, xylenes, and the like; Ethers such as DME (1,2-dimethoxyethane), isopropylether, dioxanes, diglyme, triglyme, anisol and the like; aliphatic hydrocarbons such as hexanes, heptanes, octanes, and the like; esters such as tert.butylester, isopropylester, and the like; N—$C_1$-$C_6$-alkylimidazoles, N—$C_1$-$C_6$-alkyl-1,2,4-triazoles and mixtures thereof. Preferred are toluene or xylene.

The success of the reaction according to the invention is mainly dependent on the use of the appropriate solvent, base, catalyst and reaction temperature chosen.

Process Parameters

Depending on the hydrogen pressure phenylphosphanes or cyclic phenylphosphanes are selectively obtained.

To prepare phenylphosphanes the hydrogenation process is preferably carried out at 80 to 250° C. preferably at 100-180° C., in particular at 115-160° C., and 25 to 250 bar, preferably at 50 to 250 bar hydrogen pressure.

To prepare cyclic phenylphosphanes such as tetraphenyltetraphosphetane, pentaphenyl-pentaphospholane hexaphenyl-hexaphosphorinane, the hydrogenation process is preferably carried out at 20 to 200° C. preferably at 50-180° C., in particular at 80-100° C., and 1 to 20 bar, preferably at 1 to 10. bar hydrogen pressure.

The catalyst can be separated off after the reaction by the usual methods.

The cyclic phenylphosphanes obtained in step a) or the phenylphosphanes obtained in step b) can be further reacted with acid halides R²COHal (III) to bisacylphosphanes of the formula I.

The solvents used in step c) may be, for example, the same as those used above for the first step. However, it is also possible to remove the solvent used in the first step by distillation and to take up the residue in another solvent and then to further process it. It is preferred to work in the same solvent as in the preceding step, preferably in xylene or toluene.

In step c) a base has to be added. Examples of a suitable base is NaOH, KOH, LiOH, alcoholates such as tert. butylalcoholate, tetraalkylphosphonium salts, tetraarylphosphonium salts, tetraalkylammonium salts, tetraarylammonium salts and the like.

The reaction temperatures for the reaction with the acid halide are usefully in the range from −20° to +80° C.

The bisacylphosphane of formula I can be isolated by the customary technological methods which are known to the skilled person, for example by filtration, evaporation or distillation. Likewise, the customary methods of purification may be used, for example crystallisation, distillation or chromatography.

However, the phosphanes can also be reacted without isolation to the corresponding bisacylphosphane oxides or bisacylphosphane sulfides.

Acylphosphane oxides and acylphosphane sulfides of formula IV

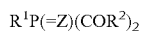

wherein $R^1$, $R^2$ are as defined above, and Z is O or S, can be prepared by oxidation or reaction with sulfur of the acylphosphane of formula I.

This process is first carried out as described above and a bisacylphosphane (I) is prepared. The crude reaction product (I) can then be further processed without purification.

It is recommended to adjust the $p_H$ of the reaction mixture prior to the oxidation step to a $p_H$ of 2-8, preferably to a $p_H$ of 3-6 by addition of typical inorganic and/or organic acids or buffer systems.

When preparing the respective oxide (Z=O), the oxidation of the phosphane (I) is carried out using the oxidant conventionally used in the technology. Suitable oxidants are in particular hydrogen peroxide and organic peroxy compounds, for example peracetic acid or t-butylhydroperoxide, air or pure oxygen.

The oxidation is usefully carried out in solution. Suitable solvents are aromatic hydrocarbons, such as benzene, toluene, m-xylene, p-xylene, ethylbenzene or mesitylene, or aliphatic hydrocarbons, such as alkanes and alkane mixtures, e.g. petroleum ether, hexane or cyclohexane. During oxidation, the reaction temperature is preferably kept in the range from 0° to 120° C., preferably from 200 and 80° C.

The reaction products can be isolated and purified by conventional processing methods known to the skilled person.

The respective sulfide is prepared by reaction with sulfur:

The bisacylphosphanes (I) are in this case reacted in substance or, where appropriate, in a suitable inert organic solvent with an equimolar to 2-fold molar amount of elementary sulfur. Suitable solvents are for example those described for the oxidation reaction. However, it is also possible to use e.g. aliphatic or aromatic ethers, such as dibutyl ether, dioxane, diethylene glycol dimethyl ether or diphenyl ether, in the temperature range from 20° to 250° C., preferably from 60° to 120° C. The resulting bisacylphosphane sulfide, or its solution, is usefully freed from any remaining elementary sulfur by filtration. After the solvent is removed, the bisacylphosphane sulfide can be isolated by distillation, chromatography or recrystallisation in pure form.

All of the above reactions are usefully carried out with exclusion of air in an inert gas atmosphere, e.g. under nitrogen or argon gas. The respective reaction mixture is usefully also stirred.

The acid halides (III), used as starting materials are known substances, some of which are commercially available, or may be prepared in analogy to known compounds.

It is characteristic of the novel process that the individual processing steps can be carried out directly one after the other without the need for isolating and purifying the respective intermediates.

The phosphane oxides and phosphane sulfides are used in the art as initiators in photopolymerisation reactions.

The following examples illustrate the invention in more detail, although it is not intended that the invention be limited to the examples. As in the remaining description and in the patent claims, parts or percentages are by weight, unless otherwise stated.

EXAMPLES

Hydrogenation of Dichlorophenylphosphane

Example 1

Preparation of pentaphenyl-pentaphospholane $(PhP)_5$

A 100 mL glass autoclave equipped with an agitator is charged with toluene (20 mL), pyridine (20 mL), palladium on activated carbon (10% Pd. 0.15 g) and dichlorophenylphosphane (1.80 g, 0.01 mol) under argon atmosphere. After rinsing the autoclave with hydrogen, the hydrogen pressure is set to 5 bar and the temperature is raised to 80° C. while stirring. After 60 hours at 80° C. and 5 bar pressure, a sample for $^{31}$P-NMR shows that all dichlorophenylphosphane has been converted to cyclophenylphosphanes $(PhP)_n$ (n=4 to 6), proportions of which can roughly be estimated by peak intensity: $(PhP)_5$ (m, −2 to −5 ppm): $(PhP)_4$ (s, −48 ppm): $(PhP)_6$ (s, −22 ppm)=38:6:1. Only traces of phenylphosphane were detected (s, −123 ppm).

Example 2

Preparation of Phenylphosphane $PhPH_2$

A 100 mL stainless steel autoclave equipped with an agitator is charged with toluene (25mL), pyridine (25 mL), palladium on activated carbon (10% Pd. 0.50 g) and dichlorophenylphosphane (4.50 g, 0.025 mol). under argon atmosphere. After rinsing the autoclave with hydrogen, the hydrogen pressure is set to 20 bar and the temperature is raised to 150° C. while stirring. When the temperature has reached 150° C., the hydrogen pressure is set to 50 bar. After 60 hours at 150° C. and 50 bar the autoclave is cooled to room temperature and a sample is taken for $^{31}$P-NMR, showing that all dichlorophenylphosphane has been converted. Phenylphosphane was the main product and only small amounts of tetraphenyl-tetra-phosphetane $(PhP)_4$ and some diphenyl-diphosphane $(PhPH)_2$ has been formed as can be estimated by peak intensity ratios: $PhPH_2$ (s, −123 ppm): $(PhP)_4$ (s, −48 ppm): meso/d,l-$(PhPH)_2$(s, −67 ppm; s, −71 ppm)=70:2:15.

Example 3

Preparation of Phenylphosphane $PhPH_2$ 50 mL of xylene, 10 mL (0.125 mol) of pyridine, 1.0 g of 10% palladium on activated carbon and 4.50 g (0.025 mol) dichlorophenylphosphane are charged into a 100 mL stainless steel autoclave equipped with an agitator under argon atmosphere. After rinsing the autoclave with hydrogen, the hydrogen pressure is set to 10 bar and the temperature is raised to 180° C. while stirring. When the temperature has reached 180° C. the hydrogen pressure is set to 50bar. After 30 hours at 180° C. and 50 bar, the autoclave is cooled to room temperature and a sample is taken for $^{31}$P-NMR spectroscopy showing that dichlorophenylphosphane has completely been converted to phenylphosphane $PhPH_2$ (s, −123 ppm).

Comparative Example According to JP2000 007689

A 100 mL glass autoclave equipped with an agitator is charged with 20 mL of DMF, 20 mL of triethylamine, 0.15 g of 10% palladium on activated carbon and 1.80 g (0.01 mol) dichlorophenylphosphane under argon atmosphere. After rinsing the autoclave with hydrogen, the hydrogen pressure is set to 5 bar and kept at 5 bar while stirring. After 4.5 hours at room temperature a sample is taken and analyzed by $^{31}$P-NMR[1] spectroscopy showing that some dichlorophenylphosphane has been converted (s, 163 ppm). The main products showed $^{31}$P-NMR signals at 77 ppm (s), 3 to −3 ppm (m), respectively. According to $^{31}$P-NMR, the reaction mass does not contain any phenylphosphane.

The hydrogen pressure is then set again to 5 bar and the temperature is increased to 50° C. After 8 hours at 50° C. and 5 bar the autoclave is cooled to room temperature and an again an analytical sample for $^{31}$P-NMR is taken. The $^{31}$P-NMR shows that all dichlorophenylphosphane has been converted and that various phosphorus containing products (s, 24 ppm; m, 11 to −5 ppm; s, 48 ppm) have been formed but still no phenylphosphane can be detected.

Hydrogenation is continued at 80° C. and 5 bar. After 23 hours, the autoclave is cooled to room temperature and a new sample is taken. $^{31}$P-NMR revealed that various phosphorus containing products (s, 67 ppm; m, 25 to 6 ppm; s, 29 ppm; s, 48 ppm; s, 49 ppm) have been formed. Phenylphosphane cannot be detected yet. A GC-MS analysis of the crude product shows the following peaks: M=181 g/mol ($C_{12}H_9NOP$), 362 g/mol, 252 g/mol ($C_{12}H_{17}N_2O_2P$), 324 g/mol, 360 g/mol ($C_{18}H_{22}N_2O_2P_2$), which indicate that reaction with the solvent DMF has been taken place.

The invention claimed is:

1. A process for the preparation of bis-acylphosphanes of formula I $R^1P(COR^2)_2$ wherein
$R^1$ is unsubstituted phenyl or phenyl substituted by one to five halogen, $C_1$-$C_8$-alkyl, $C_1$-$C_8$-alkylthio and/or $C_1$-$C_8$-alkoxy;
$R^2$ is $C_1$-$C_{18}$-alkyl or $C_2$-$C_{18}$-alkenyl; $C_1$-$C_{18}$-alkyl or $C_2$-$C_{18}$-alkenyl substituted once or more than once by halogens, —$OR^{10}$, —OCO—$R^{10}$, —OCO-Hal, —COO—$R^{10}$, —N($R^{11}$)—CO—$R^{10}$, —N($R^{11}$)—CO-Hal, —CO—$NR^{11}R^{10}$, —CH=CH—CO—$OR^{10}$ or —CH=CH-phenyl; —C($C_1$-$C_4$-alkyl)=C($C_1$-$C_4$-alkyl)-CO—$OR^{10}$ or —C($C_1$-$C_4$-alkyl)=C($C_1$-$C_4$-alkyl)-phenyl;
$C_5$-$C_{12}$-cycloalkyl, $C_2$-$C_{18}$-alkenyl, phenyl-$C_1$-$C_4$-alkyl, phenyl, naphthyl, biphenyl or a 5- or 6-membered —O—, S— or N-containing heterocyclic ring, the radicals phenyl, naphthyl, biphenyl or the 5- or 6-membered —O—, S— or N-containing heterocyclic ring being unsubstituted or substituted by one to five halogen, $C_1$-$C_8$-alkyl, $C_1$-$C_8$-alkoxy and/or $C_1$-$C_8$-alkylthio;
$R^{10}$ is hydrogen, $C_1$-$C_{18}$-alkyl, or $C_2$-$C_{18}$-alkyl which is interrupted by one or more non-successive —O-atoms, $C_5$-$C_{12}$-cycloalkyl, phenyl-$C_1$-$C_4$-alkyl, $C_2$-$C_{18}$-alkenyl, phenyl, naphthyl or biphenyl being unsubstituted or substituted by one to five $C_1$-$C_8$-alkyl, $C_1$-$C_8$-alkoxy, $C_1$-$C_8$-alkylthio and/or halogen;
$R^{11}$ is hydrogen, $C_1$-$C_{18}$-alkyl, $C_2$-$C_{18}$-alkyl which is interrupted by one or more non-successive O atoms, $C_5$-$C_{12}$-cycloalkyl, $C_2$-$C_{18}$-alkenyl, phenyl-$C_1$-$C_4$-alkyl, phenyl, naphthyl, pyridyl, the radicals phenyl, naphthyl and pyridyl being unsubstituted or substituted by one to five $C_1$-$C_8$-alkyl, $C_1$-$C_8$-alkoxy, $C_1$-$C_8$-alkylthio and/or halogen;

which process comprises
a) selective reduction by hydrogenation of dichlorophenylphosphanes of the formula II $R^1P(Cl)_2$ by means of hydrogen at a temperature in the range from 20 to 200° C. and under hydrogen pressure of atmospheric pressure to 20 bar in the presence of a hydrogenation catalyst, a tertiary aliphatic amine or an aromatic amine and in the presence of a non-protic solvent which is unreactive under the hydrogenation conditions to obtain cyclic phenylphosphanes $(R^1P)_n$ (n=4 to 6); or
b) selective reduction by hydrogenation of $R^1P(Cl)_2$ by means of hydrogen at a temperature in the range from 80 to 250° C. and under hydrogen pressure of 25 to 250 bar in the presence of a hydrogenation catalyst, a tertiary aliphatic amine or an aromatic amine and in the presence of a non-protic solvent which is unreactive under the hydrogenation conditions to obtain $R^1PH_2$;
c) subsequent reaction with an acid halide of formula III in the presence of an appropriate base $R^2$COHal
wherein $R^2$ is as defined above.

2. A process according to claim 1, wherein $R^1$ is unsubstituted phenyl and $R^2$ is phenyl which is substituted in 2,6- or 2,4,6-position by $C_1$-$C_4$-alkyl and/or $C_1$-$C_4$-alkoxy.

3. A process according to claim 2, wherein $R^2$ is 2,4,6-trimethylphenyl.

4. A process according to claim 1, comprising the steps a) and c).

5. A process according to claim 1, comprising the steps b) and c).

6. A process according to claim 1, wherein the tertiary amine is pyridine or triethylamine.

7. A process according to claim 1, wherein the non-protic solvent which is unreactive under hydrogenation reactions is selected from an aromatic hydrocarbon, an aliphatic hydrocarbon, an ether, an ester, N—$C_1$-$C_6$-alkylimidazoles, N—$C_1$-$C_6$-alkyl-1,2,4-triazoles and mixtures thereof.

8. A process according to claim 7, wherein the non-protic solvent which is unreactive under hydrogenation reactions is toluene or xylene.

9. A process according to claim 1, wherein the catalyst is selected from palladium on carbon and palladium on alumina.

10. A process according to claim 2, comprising the steps a) and c).

11. A process according to claim 2, comprising the steps b) and c).

12. A process according to claim 2, wherein the tertiary amine is pyridine or triethylamine.

13. A process according to claim 2, wherein the non-protic solvent which is unreactive under hydrogenation reactions is selected from an aromatic hydrocarbon, an aliphatic hydrocarbon, an ether, an ester, N—$C_1$-$C_6$-alkylimidazoles, N—$C_1$-$C_6$-alkyl-1,2,4-triazoles and mixtures thereof.

14. A process according to claim 12, wherein the non-protic solvent which is unreactive under hydrogenation reactions is selected from an aromatic hydrocarbon, an aliphatic hydrocarbon, an ether, an ester, N—$C_1$-$C_6$-alkylimidazoles, N—$C_1$-$C_6$-alkyl-1,2,4-triazoles and mixtures thereof.

15. A process according to claim 2, wherein the catalyst is selected from palladium on carbon and palladium on alumina.

16. A process according to claim 12, wherein the catalyst is selected from palladium on carbon and palladium on alumina.

17. A process according to claim 14, wherein the catalyst is selected from palladium on carbon and palladium on alumina.

18. A process according to claim 1 wherein the hydrogenation catalyst comprises a metal, metal oxide or Raney form of metal wherein the metal is selected from ruthenium, rhenium, rhodium, platinum, palladium, copper, nickel, cobalt and molybdenum or the hydrogenation catalyst is copper chromite.

19. A process according to claim 18 wherein the catalyst is supported on carbon, niobium, titania, zirconia, silica, tin, alumina or mixtures thereof.

* * * * *